US009048541B2

United States Patent
Li et al.

(10) Patent No.: US 9,048,541 B2
(45) Date of Patent: Jun. 2, 2015

(54) INVERTED E ANTENNA WITH CAPACITANCE LOADING FOR USE WITH AN IMPLANTABLE MEDICAL DEVICE

(75) Inventors: Perry Li, Temple City, CA (US); Gabriel A. Mouchawar, Valencia, CA (US); Jorge Amely-Velez, Simi Valley, CA (US); Reza Imani, Moorpark, CA (US)

(73) Assignee: PACESETTER, INC., Sylmar, CA (US)

( * ) Notice: Subject to any disclaimer, the term of this patent is extended or adjusted under 35 U.S.C. 154(b) by 169 days.

(21) Appl. No.: 13/538,501

(22) Filed: Jun. 29, 2012

(65) Prior Publication Data

US 2014/0002314 A1 Jan. 2, 2014

(51) Int. Cl.
*H01Q 1/12* (2006.01)
*H01Q 1/36* (2006.01)
*H01Q 1/24* (2006.01)
*H01Q 1/27* (2006.01)
*H01Q 1/22* (2006.01)
*H01Q 9/42* (2006.01)
*A61N 1/372* (2006.01)

(52) U.S. Cl.
CPC . *H01Q 1/36* (2013.01); *H01Q 1/24* (2013.01); *H01Q 1/273* (2013.01); *H01Q 1/22* (2013.01); *H01Q 9/42* (2013.01); *A61N 1/37229* (2013.01)

(58) Field of Classification Search
CPC ....... H01Q 1/273; H01Q 9/0421; H01Q 1/36; H01Q 1/40; H01Q 9/42; H01Q 1/00; H01Q 1/24; H01Q 1/27; H01Q 9/26; H01Q 1/22
USPC .......................................... 343/702, 718, 873
See application file for complete search history.

(56) References Cited

U.S. PATENT DOCUMENTS

| 5,720,767 | A | | 2/1998 | Amely-Velez | |
|---|---|---|---|---|---|
| 5,821,907 | A | * | 10/1998 | Zhu et al. | 343/906 |
| 6,025,805 | A | * | 2/2000 | Smith et al. | 343/702 |
| 7,047,076 | B1 | * | 5/2006 | Li et al. | 607/36 |
| 7,467,014 | B2 | * | 12/2008 | Fuller et al. | 607/60 |
| 7,844,341 | B2 | * | 11/2010 | Von Arx et al. | 607/60 |
| 7,903,043 | B2 | * | 3/2011 | Rawat et al. | 343/873 |
| 8,588,924 | B2 | * | 11/2013 | Dion | 607/60 |
| 2004/0227672 | A1 | * | 11/2004 | Chen et al. | 343/702 |
| 2012/0001812 | A1 | * | 1/2012 | Zhao et al. | 343/718 |
| 2012/0165885 | A1 | * | 6/2012 | Lavie | 607/5 |

OTHER PUBLICATIONS

King, Harrison, Denton, Transmission-Line Missile Antennas, 1960, Inst. Radio Eng., vol. ap8, pp. 88-90.*

* cited by examiner

*Primary Examiner* — Dameon E Levi
*Assistant Examiner* — Hasan Islam

(57) ABSTRACT

The device includes radio frequency (RF) communication components installed within a case of the device and an antenna with an inverted E shape mounted within a header of the device. The antenna has three branches extending from a main horizontal arm: a capacitive branch connecting one end of the main arm to the case via a capacitive load; an RF signal feed branch connecting a middle portion of the main arm to the internal RF components of the device via a feedthrough; and an inductive branch connecting the opposing (far) end of the main arm to the case to provide a shunt to ground. The E-shaped configuration and the provision of capacitive loading allows for cancellation of inductance to bring the antenna into resonance and to provide optimal radiation efficiency as well as to provide for impedance with no reactive component.

20 Claims, 10 Drawing Sheets

INVERTED E ANTENNA WITH CAPACITANCE LOADING FOR USE WITH AN IMPLANTABLE MEDICAL DEVICE

FIELD OF THE INVENTION

The invention generally relates to implantable medical devices, such as pacemakers and implantable cardioverter/defibrillators (ICDs), and in particular to antennas for use therein.

BACKGROUND

State-of-the-art pacemakers, ICDs and other cardiac rhythm management devices (CRMDs) can be equipped with radio-frequency (RF) communication devices for communicating with external systems such as bedside monitors or external diagnostics systems. In particular, RF communication devices have been developed to utilize Medical Implant Communication Service (MICS)-band radio transmissions or Medical Device Radiocommunications Service (MedRadio)-band transmissions. (MedRadio maintains the spectrum previously allocated for MICS (402-405 MHz) while adding additional adjacent spectrum (401-402 MHz and 405-406 MHz).) Herein, the term "MICS/MedRadio" will be used for the sake of completeness and generality to refer to MICS, MedRadio or both.) RF capable devices use an antenna within the header or adjacent header for receiving or transmitting RF signals. However, problems arise in designing such antennas due to the increasing miniaturization of CRMDs and their components.

In particular, there can be a loss of RF communication performance due to the reduction in size of the header and the device case (also called the housing or the "can") of the CRMD. As technology improves, the sizes of the implantable devices continue to shrink but the laws of physics regarding RF communications do not change. Since about 2005, at least some CRMD designers have employed a shorted loop antenna for RF communications. However, RF computer simulations indicate that a further reduction in device size would diminish antenna performance below acceptable levels. Accordingly, there is a need to provide improved antenna designs for use with CRMDs, especially relatively small devices.

In this regard, there are many challenges to designing a well performing antenna for use within an implantable medical device. One issue is the significant amount of attenuation inherent to the system since the RF signal travels through the lossy human body. Another problem is that the size of the antenna is limited by the size of the header (at least for devices where the antenna is to be fitted inside the header.) Ideally, the antenna should have a length equal to a quarter wavelength of the operating frequency (which is typically near 400 MHz), but it is difficult to design an antenna that fits within a device header while achieving that length. Hence, for antennas to be housed in the device header, the quarter wavelength constraint can result in an antenna much smaller than needed for optimum performance. Another issue is that the antenna should have an input impedance that is the complex conjugate of impedance of the internal circuitry of the device so maximum power transfer can take place. If the impedance of the antenna is too low or too high, additional mismatch losses will occur, which will decrease signal power.

FIG. 1 illustrates an antenna 2 that attempts to meet these requirements using a folded monopole design commonly known as an "Inverted L antenna" for use within the header 4 of an exemplary CRMD 6. The Inverted L is a monopole that ideally should be sized to a quarter wavelength of its operating frequency with a 90-degree bend to resemble a downward facing L. The antenna can fit within a fairly small header volume but suffers from very low input impedance. Also, this antenna is best suited for higher gigahertz (GHz) frequency applications where the necessary antenna length for resonance is relatively short. At 400 MHz, implementing an Inverted L antenna becomes impractical for implantable device purposes, as this would require a very long antenna that would not fit within the header. To solve the impedance issue, an extra branch 7 can be connected to the Inverted L and shunted to ground. This topology, shown in FIG. 2, is known as the "Inverted F antenna." (An Inverted F antenna design is discussed, for example, in U.S. Pat. No. 7,047,076 to Li et al., entitled "Inverted-F Antenna Configuration for an Implantable Medical Device.") The extra shunt connection provides a larger input impedance for matching purposes but the Inverted F still suffers from lack of adequate length for practical applications wherein the antenna must fit within the header of a relatively small CRMD.

Accordingly, there is a need to provide an improved antenna, particularly for MICS/MedRadio applications, that addresses these and other issues. It is to this end that aspects of the invention are generally directed.

SUMMARY

In accordance with an exemplary embodiment, an implantable medical device is provided for implant within a patient wherein the device includes RF communication components installed within a case of the device. An antenna having an inverted E shape is coupled to the RF communication components. The inverted E shape of the antenna incorporates many of the aforementioned benefits of an inverted F antenna while providing, in preferred embodiments, for capacitive loading to allow for tuning of impedance and resonance frequency. In an illustrative embodiment, the inverted E antenna is installed within a header mounted to an exterior of the case of the implantable device. The case provides a ground plane for the antenna. The antenna has three branches extending from a main horizontal arm that forms the base of the inverted "E." The three branches include: a first "capacitive branch" connecting one end of the main arm to the case via a capacitive load; a second "RF signal feed branch" connecting a middle portion of the main arm to the internal RF components of the device via a feedthrough (or feedthru) in the case; and a third "inductive branch" connecting the other end of the main arm to the case to provide a shunt to ground. Note that, at MICS frequencies, a shunt (depending on its dimensions) may behave like a small inductor and hence the third branch that is shunted to ground is referred to as the inductive branch. At resonance, the capacitive loading of the first branch cancels the inductance of the third branch to provide optimal radiation efficiency as well as to provide a real impedance with no reactive (i.e. imaginary) component.

In one particular example, the capacitive branch of the antenna includes a capacitor (or other means for providing capacitance) mounted in series between the main arm and a distal end of the branch that is coupled to the case of the device. During device design, the value of the capacitor can be selected in conjunction with other antenna design parameters to substantially cancel any inductance provided by the antenna or to achieve other goals. In particular, by properly selecting the capacitance, the resonant frequency of the antenna can be set to the operating frequency of the device to provide both very good impedance and very good performance without having to change the length or height of the antenna. In another example, the capacitive branch includes a parallel plate mounted via an epoxy dielectric (or other suitable material) to the case of the device so that the plate, the epoxy and the adjacent portion of the case collectively form a plate capacitor. During device design, the capacitance can be set by selecting the size of the plate, the distance from the plate to the case and the electrical characteristics of the dielectric epoxy. In yet another example, the capacitive branch includes a discoidal capacitor mounted within the case via a secondary feedthrough. During design, the value of the discoidal capacitor can be selected in conjunction with other antenna design parameters so as to substantially cancel any inductance or to achieve other goals. In some examples, the antenna might contain non-metallic elements (such as highly conductive fluids.)

In the illustrative embodiment, the middle RF signal feed branch of the antenna is coupled to the internal RF communication components within the case via the primary feedthrough. In one particular example, the primary feedthrough includes an inner conducting pin, an outer conductor grounded to the case and a dielectric material separating the inner pin from the outer conductor. The inner pin is connected to a terminal of the internal RF components. As to the inductive branch of the antenna, it is mounted directly to the case for providing the shunt to ground. The overall inductance of the antenna can be set during device design by selecting the length of the inductive branch relative to the lengths of the other branches of the antenna.

With this inverted E configuration, the impedance and resonance frequency of the antenna can thereby be set easily during design to preferred or optimal values by selecting the capacitance provided by the first branch, the inductance provided by the third branch and the location of the middle RF signal feed branch relative to the first and third branches. Indeed, any change to the length and cross-sectional area of the antenna can be seen as a change in inductance, which can be canceled out with a corresponding change in the capacitor. Thus, if the latest model of the implantable device is made smaller (requiring a smaller antenna), suitable adjustments to the design of the inverted E type antenna can be made to maintain preferred or optimal impedance values. That is, impedance can be tuned to match device circuitry. In some examples, the antenna is configured to provide an impedance of about 50 ohms with substantially no reactive components. Hence, the inverted E-shaped antenna and its components allow for great flexibility during device design to achieve operational or performance goals. Also, by allowing for a generally smaller antenna, the header can be made smaller, thus making the overall device smaller and lighter. The antenna may be used either for transmitting or for receiving RF signals. That is, by virtue of the reciprocity theorem, the antenna is equally effective at receiving and transmitting signals. Implantable devices incorporating the antenna may be implemented using a bi-directional half duplex protocol to accommodate both reception and transmission.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description that follows, like numerals or reference designators will be used to refer to like parts or elements throughout.

Overview of Implantable System

Figure 1:
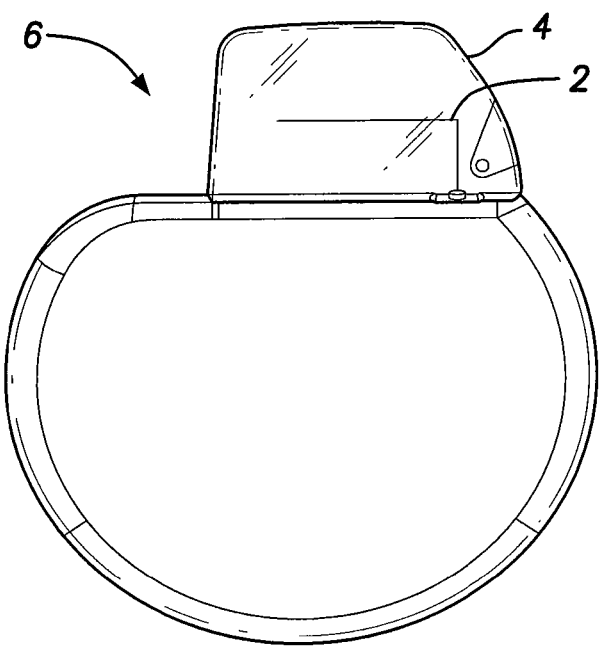
FIG. 1 illustrates a conventional inverted L antenna mounted within the header of an implantable medical device.
Figure 2:
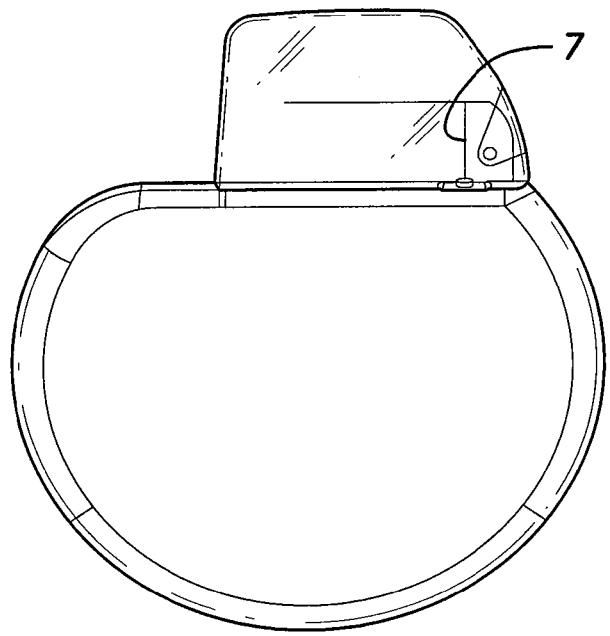
FIG. 2 illustrates a conventional inverted F antenna mounted within the header of an implantable medical device.
Figure 3:
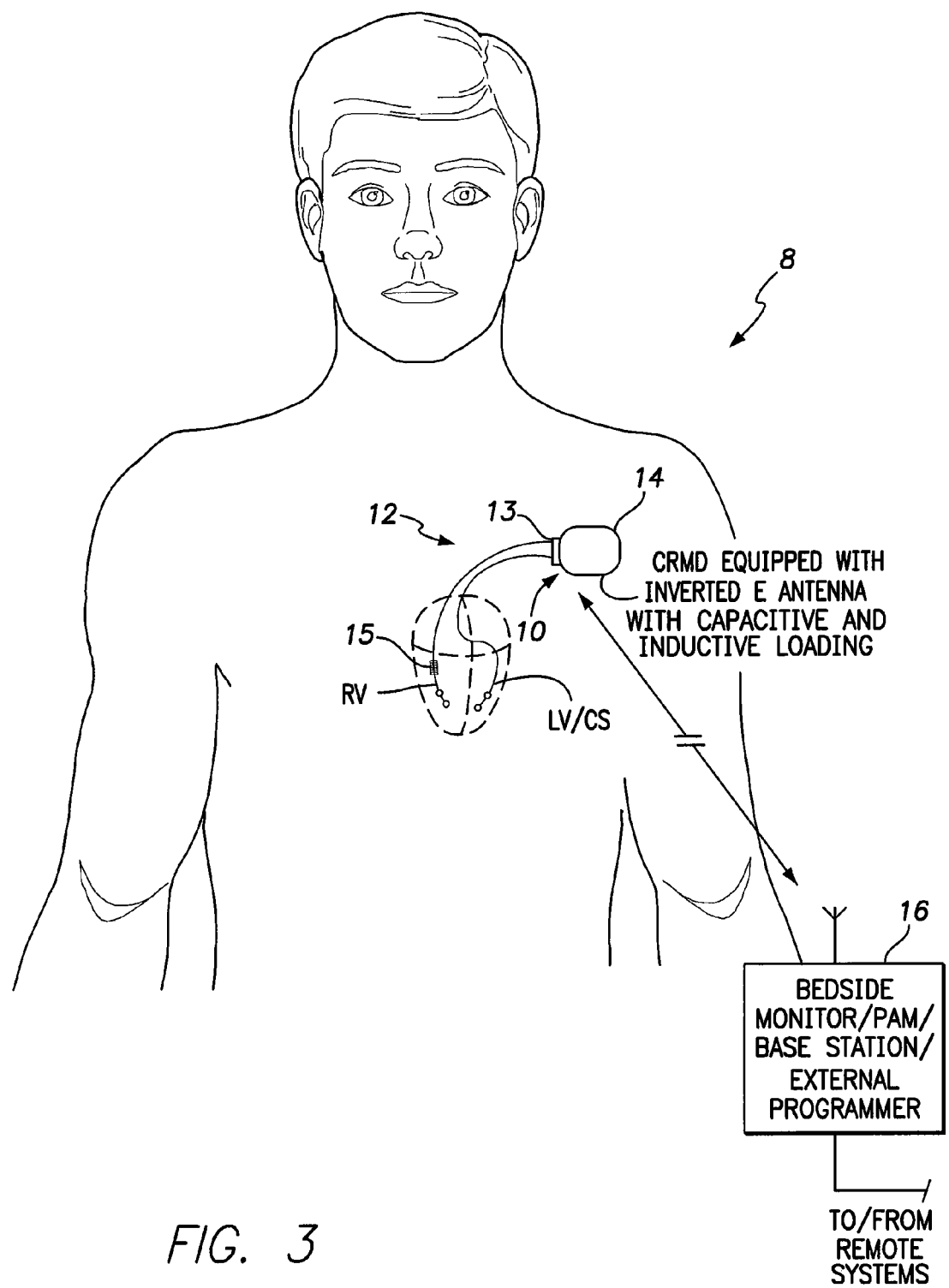
FIG. 3 illustrates pertinent components of an implantable medical system having an CRMD equipped for MICS/MedRadio communication and incorporating an inverted E antenna (mounted within a header of the device) that includes capacitive and inductive loading.
Figure 10:
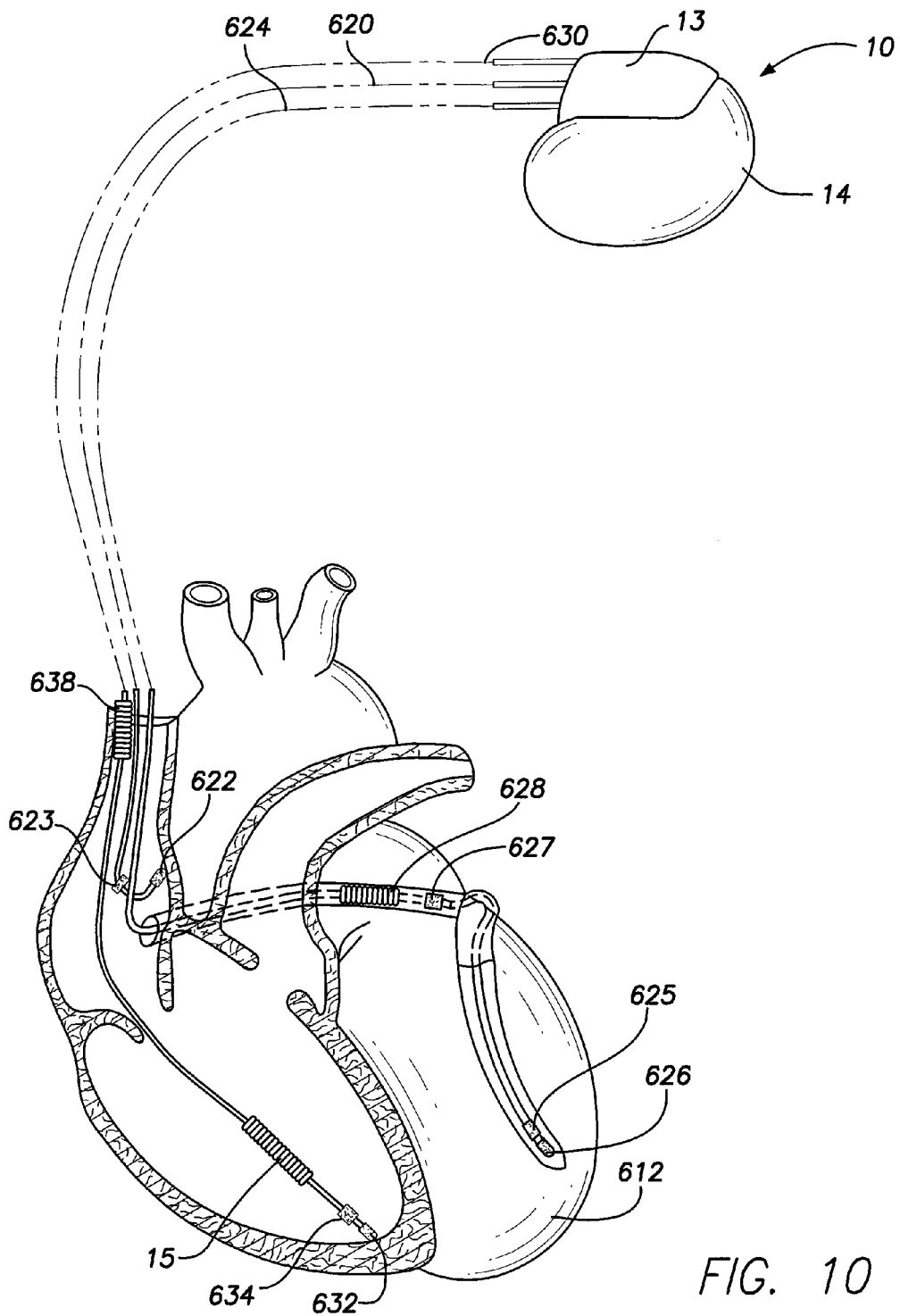
FIG. 10 is a simplified, partly cutaway view, illustrating the CRMD of FIG. 3 along with a set of leads implanted on or in the heart of the patient.

FIG. 3 illustrates an implantable medical system 8 having a CRMD 10 equipped with an inverted E antenna (not specifically shown in FIG. 3 but shown in FIGS. 4-8) for use with MICS/MedRadio transmissions and further equipped with one or more cardiac sensing, pacing and/or shocking leads 12 implanted within the heart of the patient. In some examples, the CRMD may be equipped to perform both pacing and shocking functions and may be referred to as a hybrid pacemaker/ICD or just a "hybrid." In FIG. 3, two exemplary leads are illustrated: a bipolar RV lead and a bipolar left ventricular (LV) lead implanted via the coronary sinus (CS). An RA lead may also provided that includes a bipolar RA tip/ring pair. Other suitable leads may instead be employed, including leads with more or fewer electrodes such as quadripolar leads. Also, as shown, the exemplary RV lead has an RV coil 15 implanted within the RV for delivery of defibrillation shocks (for examples wherein the CRMD is equipped to operate as an ICD.) Other electrodes of various sizes and shapes may be additionally or alternatively provided such as an LV coil. A more complete set of leads is illustrated in FIG. 10. The inverted E antenna is installed with a header 13 mounted to an end of the case 14 (also referred to as the housing or can) of the CRMD. The header also provides connection terminals for leads 12.

MICS/MedRadio components within CRMD 10 use the inverted E antenna for communicating with an external system 16 via RF signals. External system 16 may include, for example, an external programmer, bedside monitor, base station or hand-held personal advisory module (PAM). The MICS/MedRadio components may exploit InvisiLink™ Wireless Telemetry of St. Jude Medical. For example, periodic transfers for diagnostics data may be transmitted from the CRMD to a bedside monitor located within about two meters of the patient. Data from the external system can then be forwarded to a centralized system such as the Merlin.Net system, the HouseCall™ remote monitoring system or the Merlin@home systems of St. Jude Medical so as to relay the information to a clinician.

Note that CRMD 10 can be any suitably-equipped device such as a standalone pacemaker, ICD or cardiac resynchronization therapy (CRT) device, including CRT-D and CRT-P devices) or combinations thereof. CRMDs are generally discussed, for example, in U.S. Pat. No. 5,720,767 to Amely-Velez, entitled "Impedance Dependent Implantable Cardioverter-Defibrillator." Moreover, although identified in FIG. 3 as a CRMD, it should be understood that device 10 can comprise other implantable medical devices such as neural stimulation devices or the like. The aforementioned inverted E antenna is particularly useful for MICS and/or MedRadio communications but may be useful for other purposes as well. Furthermore, it should be understood that the particular shape, size and locations of the implanted components shown in FIG. 3 are merely illustrative and may not necessarily correspond to actual implant locations. In particular, preferred implant locations for the leads are more precisely illustrated in FIG. 10.

Inverted E Antenna

Figure 4:
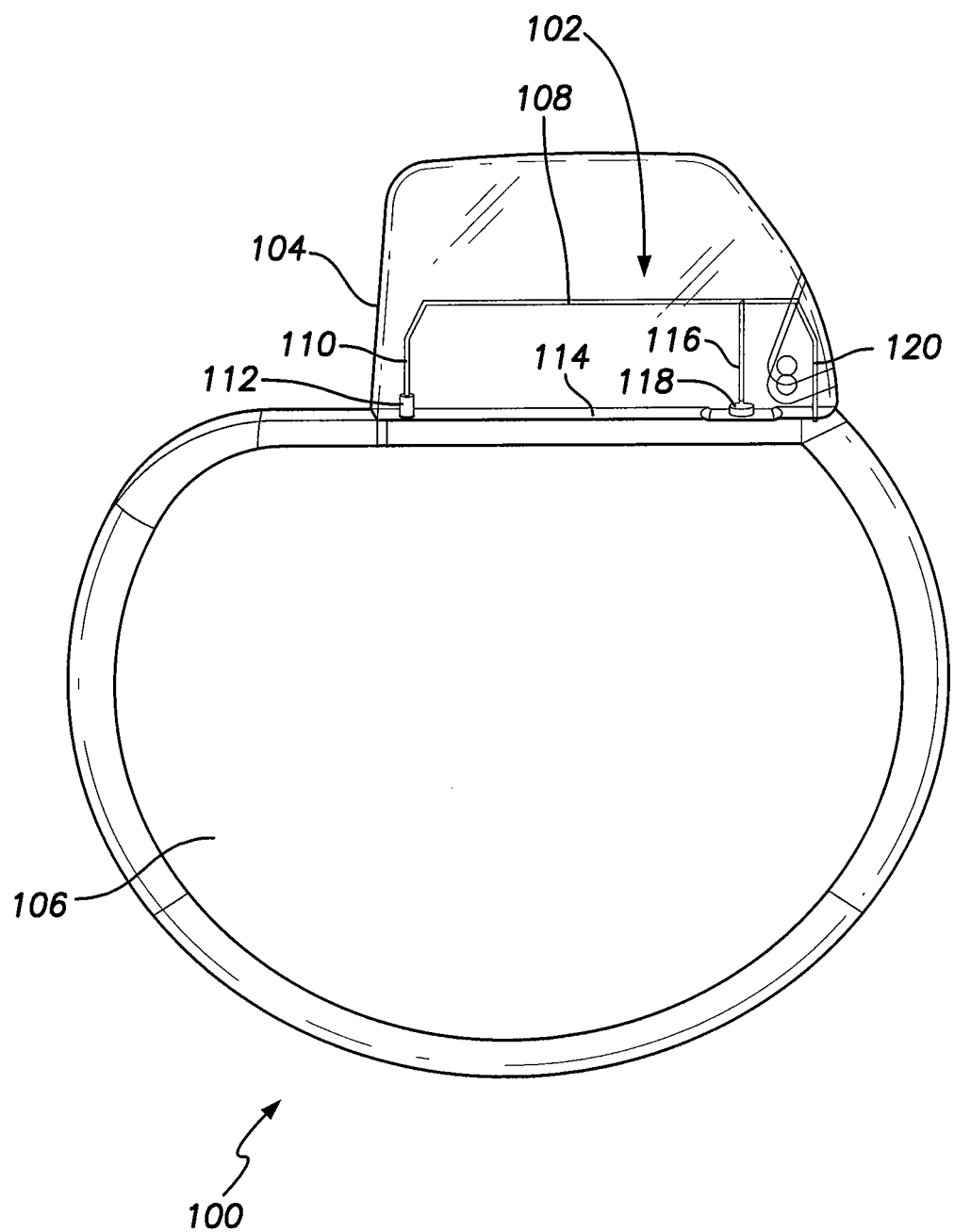
FIG. 4 illustrates the inverted E antenna of the CRMD of FIG. 3 mounted within the header of an implantable medical device.

FIGS. 4-8 illustrate various examples of the inverted E antenna, which is mounted within the header of the device. Referring next to FIG. 4, CRMD 100 includes an inverted E antenna 102 installed within header 104 mounted to the case (or housing or can) 106 of the device. The case provides a ground plane for the device. In the figure, the header is transparent simply to permit illustration of the antenna. The antenna includes a conducting main arm 108 that provides the "backbone" for the antenna. Three conducting branches extend from main arm 108 for connecting to the case or its internal components. In particular, a capacitive branch 110 extends from a first end of the main arm and includes a capacitor 112 mounted along a distal end of the branch, which is in turn electrically coupled to a conducting surface 114 inside the header. An RF signal feed branch 116 extends from a middle or central portion of the main arm and is electrically coupled to internal RF components of the device via a feedthrough 118. An inductive branch 120 extends from a second end of the main arm and is directly connected to conducting surface 114 to provide a shunt to ground. Branch 120 is referred to herein as an inductive branch since its length can be adjusted during antenna design to vary the inductance of the antenna to help achieve a desired impedance. In other examples, an actual inductor might be mounted to branch 120 (or elsewhere on the antenna) to provide additional impedance, if desired.

Note that due to the nature of how this antenna works, the RF feed should be the middle branch in the E structure. However, the RF signal feed branch need not be connected at the center of the main arm and, as shown, can be mounted closer to one end or the other, as appropriate. The electrical characteristics of the antenna can be adjusted, in part, based on the relative location of the middle branch along the main arm. In the particular example of FIG. 4, the RF signal feed branch is mounted closer to the inductive branch than the capacitive branch. The positions and lengths of the shunt and capacitive branches will depend upon the form factor of the header and what is required for optimum performance. Although not shown in FIG. 4, additional components may be mounted within the header, such as mounting devices (discussed below) for connecting to the proximal ends of pacing or sensing leads. Note also that the wire antenna itself can have a rectangular or circular cross section depending on what is preferable to meet size and performance requirements.

Figure 5:
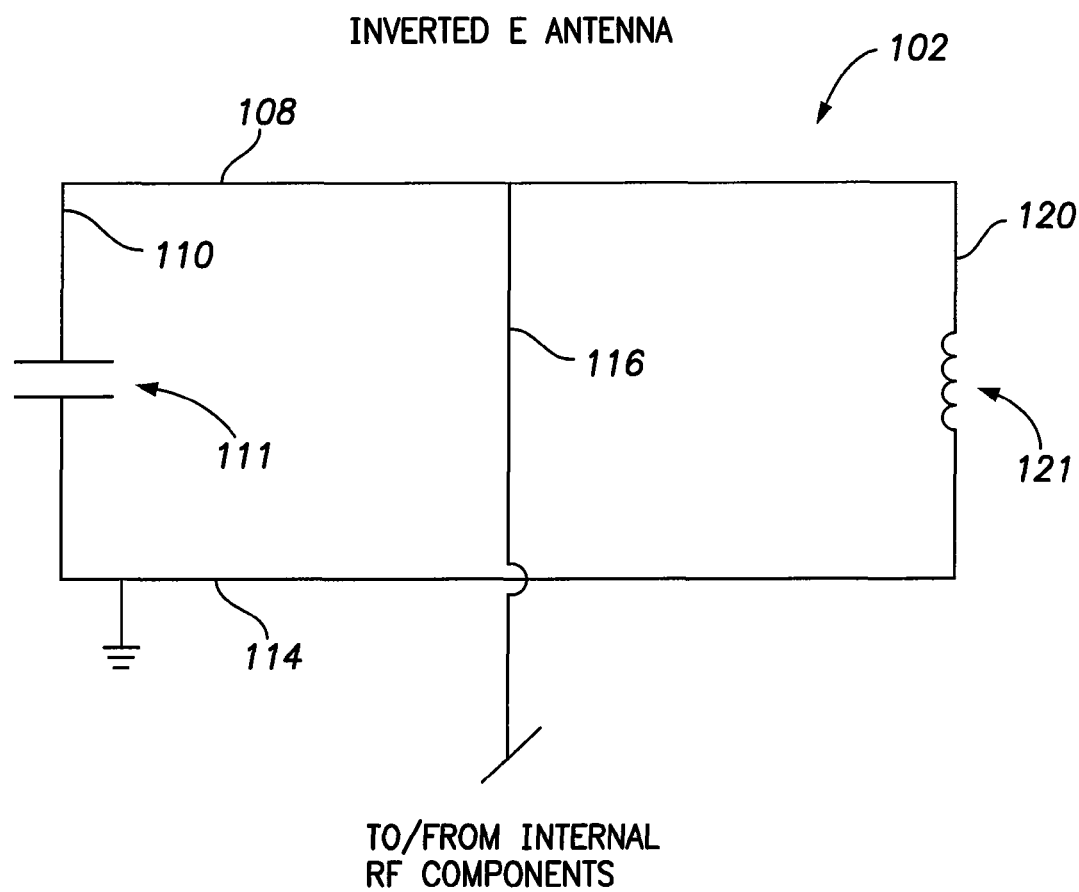
FIG. 5 is a schematic of the inverted E antenna of FIG. 4.

FIG. 5 provides a schematic illustration of the antenna circuit. Briefly, antenna 102 includes first branch 110 connected to ground 114 for providing capacitance 111, second branch 116 connected directly to internal RF components of the device for providing a signal feed, and third branch 120 connected to ground for providing inductance 121, where each of the branches is also connected as shown to main conducting arm 108. In some examples, the capacitance and inductance are set to provide an impedance of about 50 ohms with substantially no imaginary components (at least at MICS or MedRadio operating frequencies such as 400 MHz.)

Figure 6:
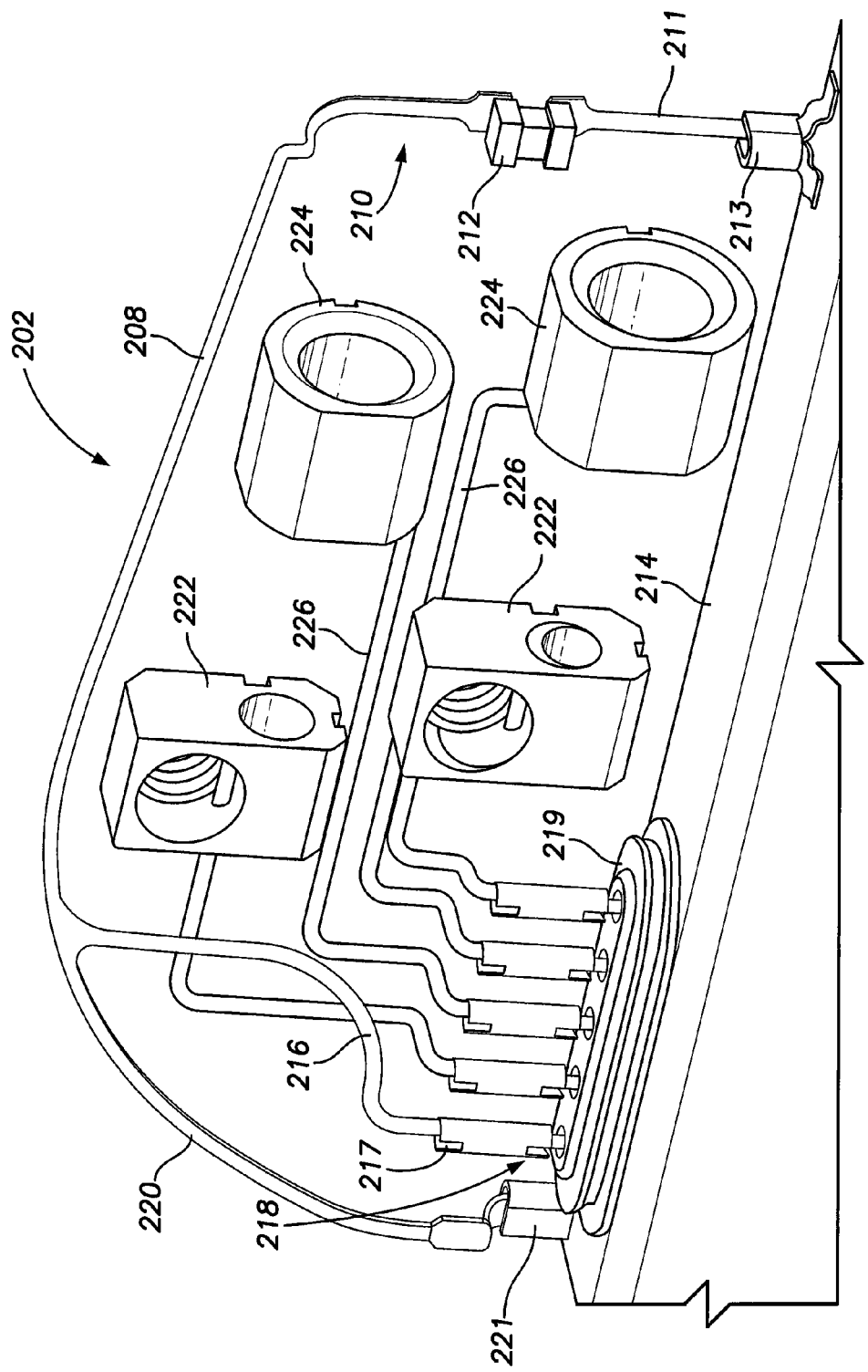
FIG. 6 illustrates an alternative embodiment of the inverted E antenna of FIG. 4 wherein the branches are curved.

FIG. 6 illustrates an exemplary inverted E antenna 202 in greater detail along with other components that may be installed within a device header for coupling to pacing, sensing and/or shocking leads. The antenna again includes a main arm 208 along with three conducting branches. A capacitive branch 210 includes a discrete surface mount technology (SMT) capacitor 212 mounted in series between arm 208 and an RF case connector 213 mounted to conducting surface 214 inside the header (where the header is not shown in this illustration.) An RF signal feed branch 216 is connected from a middle portion of arm 208 to internal RF components of the device via an RF lead connection 217 mounted to a feedthrough channel 218 of a main feedthrough assembly 219. (Feedthrough 218 can include an outer conductor which is grounded to the can, an inner conductor which is a pin running though the center of the feedthrough, and a dielectric material that separates the inner and outer conductor. Inside the can, the feedthrough pin connects to the RF circuitry and transceiver.) An inductive branch 220 extends from main arm 208 and is connected to conducting surface 214 via an RF case connector 221 to provide a shunt to ground. Additionally, FIG. 6 shows components 222 and 224 for connecting proximal ends of the aforementioned leads to internal components of the CRMD via various connection lines 226 via feedthrough assembly 219. In one example, components 222 are ring connectors for connecting to conductors within the leads that couple to ring electrodes at the distal ends of the leads. Components 224 are tip connectors for connecting to conductors of the leads that couple to tip electrodes at the distal ends of the leads.

In one particular example, the following sizes and dimensions are used: inductive branch 220, main arm 208 and the portion of capacitive branch 210 leading to capacitor 212 are referred to collectively as Antenna Part A and have an overall length of 1.8" (i.e. 1.8 inches) and a thickness of 0.10"; RF signal feed branch 216 is referred to as Antenna Part B and has a length of 0.5" and a thickness of 0.10"; capacitive branch portion 211 connecting capacitor 212 to connector 213 is referred to as Antenna Part C and has a length of 0.3" and a thickness of 0.10". Capacitor 212 has a case size designator of "0805" (with dimensions of 079" by 0.049" by 0.051") and provides a capacitance of about 2.7 picoFarads (pF.) With this overall configuration, the antenna inductance is about 58.6 nanoHenries (nH.) It should be understood that these are just exemplary values for one example. Other dimensions and components would be used with differing values for capacitance and inductance in other examples. Still further, rather than using wires to form the main arm and branches of the antenna, other conducting elements might be used, including elements incorporating conducting fluids. Preferably, the capacitor is implemented so that it can be altered if the impedance or resonance frequency of the rest of the antenna changes during device design. In the example of FIG. 6, this would be accomplished by replacing capacitor 212 with a different capacitor providing a different amount of capacitance.

Figure 7:
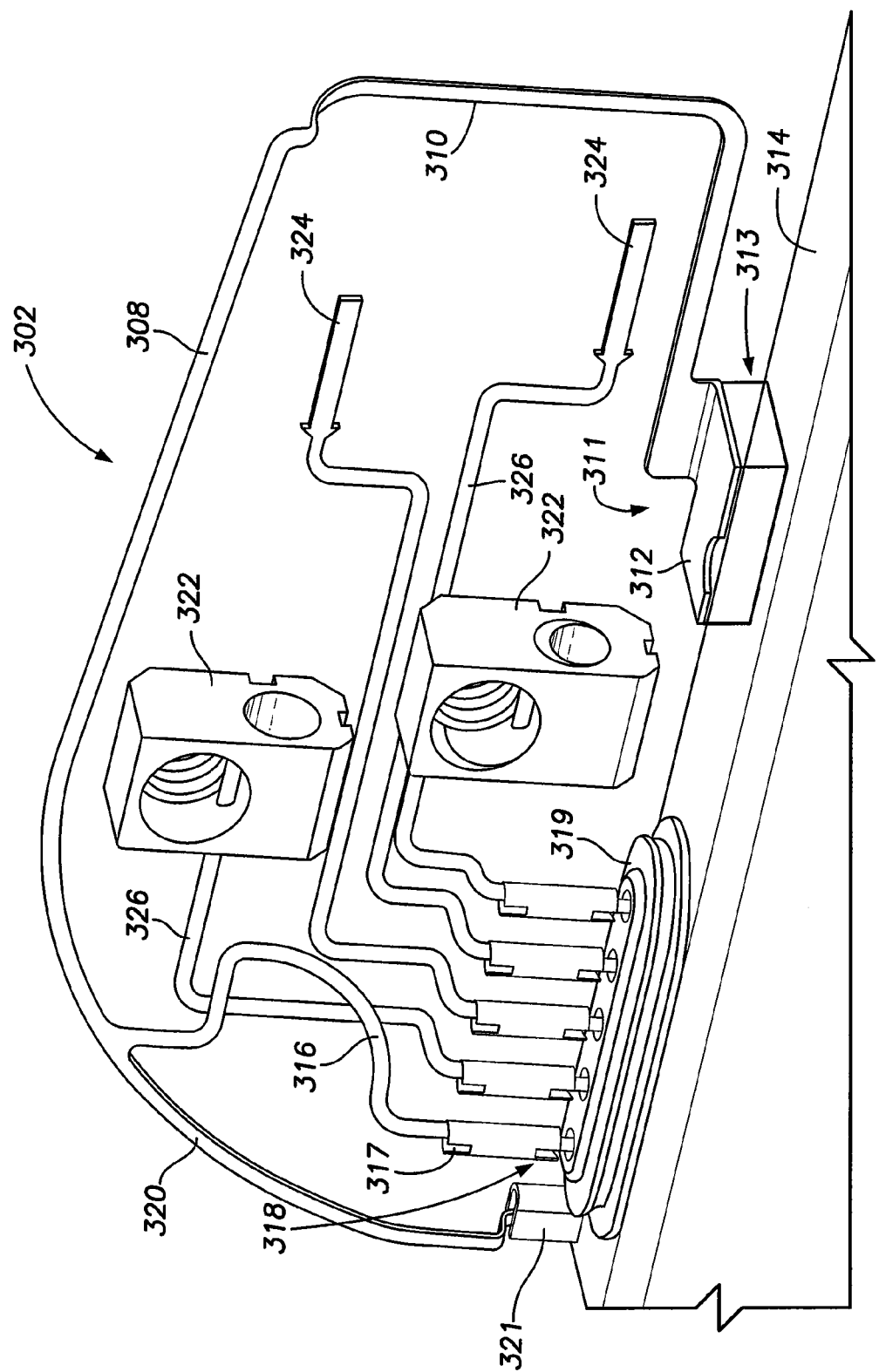
FIG. 7 illustrates another embodiment of the inverted E antenna of FIG. 4 wherein an capacitor integrated plate is employed.

FIG. 7 illustrates an exemplary inverted E antenna 302 that includes an integrated parallel plate capacitor. Many of the features of antenna 302 are the same or similar to that of antenna 202 and hence will not be described again in detail. Antenna 302 includes a main arm 308 and three branches: a capacitive branch 310; an RF signal feed branch 316 connected to internal RF components via a connector 317 mounted to feedthrough channel 318 of main feedthrough assembly 319; and an inductive branch 320 connected to surface 314 via electrical connector 321 to provide a shunt to ground. In this example, however, rather than installing a capacitor along the capacitive branch, an end of the branch provides an integrated capacitor 311. That is, a distal end of branch 310 includes a plate portion 312, which is mounted via a dielectric epoxy 313 (or another suitable plastic material) to surface 314 to provide capacitance. FIG. 7 also shows components 322 for lead connection. To more clearly show the parallel plate capacitor, FIG. 7 does not show devices corresponding to components 224 of FIG. 4 but instead just shows connection terminals 324. Note that the presence of metal devices in close proximity to the antenna (such as various tip and ring connectors) could affect the operation of the antenna and hence should be taken into account during antenna design to achieve a desired impedance and resonance frequency. This is particularly true in designs where the capacitor is not isolated from the outside environment (as in FIG. 7.) For cases where the capacitor is packaged (FIGS. 6 and 8), metal components near the antenna should have negligible impact.

In one particular example, the following sizes and dimensions are used: inductive branch 320, main arm 308 and capacitive branch 310 are referred to collectively as Antenna Part A and have an overall length of 2.2" and a thickness of 0.10"; and RF signal feed branch 316 is referred to as Antenna Part B and has a length of 0.5" and a thickness of 0.10". The epoxy used for dielectric 313 is HYSOL EE0079/HD0070 made by Loctite™ and provides a dielectric constant of about 3.8. In the example where HYSOL EE0079/HD0070 is used, plate 312 has dimensions of 0.100" by 0.260" with a plate thickness of about 0.010" and is mounted at a distance of 0.038" from surface 314 to provide a plate capacitance of about 1.3 pF. With this overall configuration, the antenna inductance is about 121 nH. Note that by varying the area of the plate and the distance between the plate and housing (as well as the type of epoxy); different capacitance values can be achieved. In particular, if the impedance or resonance frequency of the antenna changes during device design, the spacing between the plate and the case could be changed to provide a different capacitance.

Figure 8:
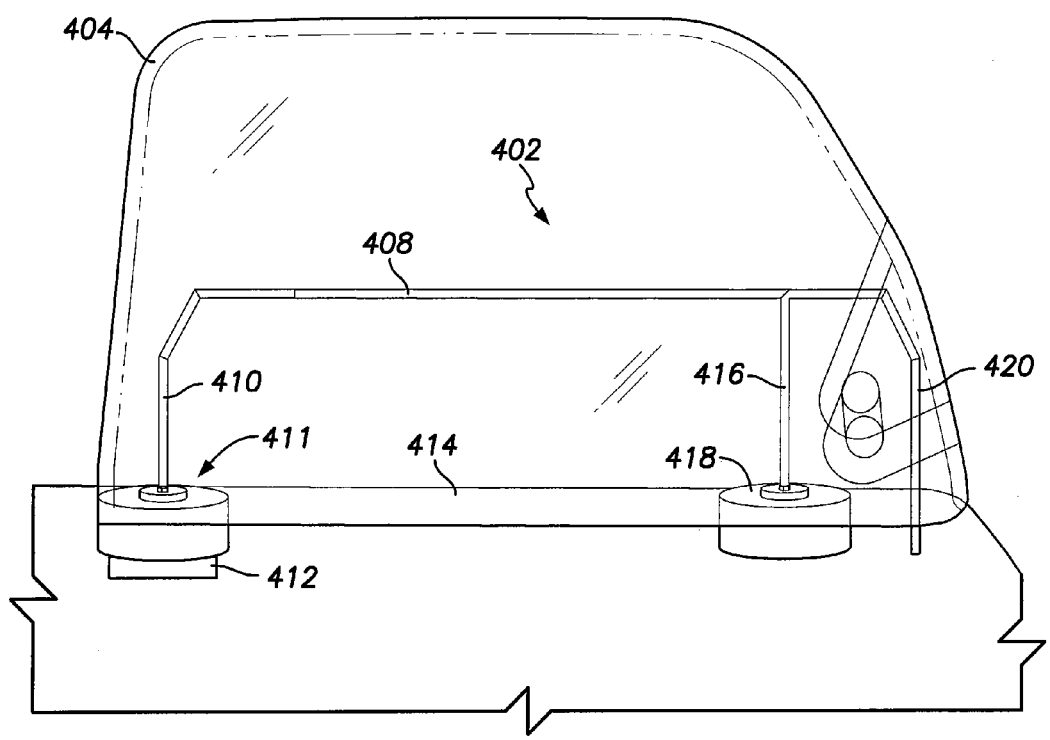
FIG. 8 illustrates yet another embodiment of the inverted E antenna of FIG. 4 wherein a discoidal capacitor is employed.

FIG. 8 illustrates an exemplary inverted E antenna 402 that includes a discoidal capacitor. Many features are the same or similar to those already described and hence will not be described again in detail. Antenna 402 is mounted within a header 404 (shown transparent to permit illustration of the antenna.) The antenna again includes a main arm 408 and three conducting branches: a capacitive branch 410; an RF signal feed branch 416 connected to internal RF components via a feedthrough 418; and an inductive branch 420 to provide a shunt to ground. In this example, however, rather than installing a capacitor along the capacitive branch inside the header, the capacitor is mounted inside the case. That is, an end of branch 410 extends through case surface 414 via a feedthrough 411 to a first terminal of a discoidal capacitor 412 (shown extending below the outer flange 413 of the feedthrough, which is mounted to an interior surface of the case. A second, opposing terminal of the capacitor is electrically connected to the interior of the case. With this configuration, although the capacitor is mounted inside the case, it is still connected in series between the main arm of the antenna and the case (which provides the ground plane for the device.) That is, the antenna functions in the same manner as shown in FIG. 5. Nevertheless, by positioning the capacitor inside the case rather than inside the header, the capacitor does not take up space within the header. In one particular example, discoidal capacitor 412 is a multi-layer ceramic capacitor providing a capacitance of 10 pF and the other antenna components are configured to yield an overall inductance of 15.8 nH.

Figure 9:
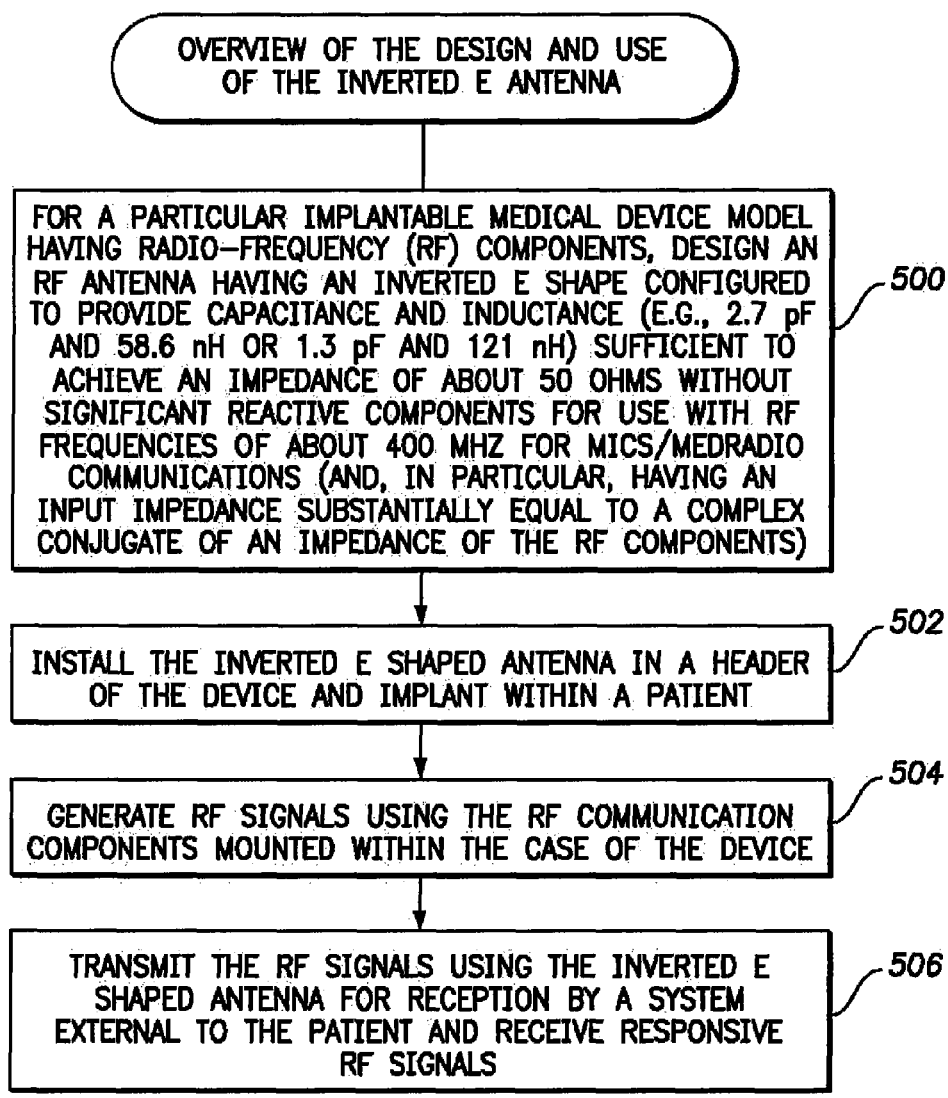
FIG. 9 illustrates exemplary techniques pertaining to designing and using the inverted E antenna of FIGS. 3-8.

FIG. 9 broadly summarizes a procedure for designing and using an inverted E antenna. Briefly, at step 500, for a particular implantable medical device model having RF components, an RF antenna having an inverted E shape is designed and configured to provide capacitance and inductance sufficient to achieve an impedance of, in one example, about 50 ohms without significant reactive components for use with RF frequencies of about 400 MHz for MICS/MedRadio communications (and, in particular, having an input impedance substantially equal to a complex conjugate of an impedance of the RF components.) The exemplary capacitance and inductance values discussed above are listed in FIG. 9. In other examples, different values might be used to achieve a different impedance. At step 502, the inverted E shaped antenna is installed in a header of the device and implanted within a patient. At step 504, RF signals are generated using RF communication components mounted within the case of the device and, at step 506, the RF signals are transmitted using the inverted E shaped antenna for reception by a system external to the patient. Signals generated by the external system may also be received by the antenna and routed to the internal RF components of the implanted device for use in controlling the operation of the device. The broad summary of FIG. 9 does not, of course, set forth all steps that may be needed. In particular, approval by the U.S. Food and Drug Administration (FDA) or other regulatory authorities may be required before implant of the device within a patient.

Although primarily described with respect to examples wherein the implanted device is a CRMD, other implantable medical devices may be equipped to exploit the techniques described herein. Where appropriate, the antenna described herein may be used in conjunction with other antenna design features. See, for example, shielding features described in U.S. patent application Ser. No. 13/458,934 of Amely-Velez et al., filed Apr. 27, 2012, and entitled "Electromagnetic Interference Shielding for use with an Implantable Medical Device Incorporating a Radio Transceiver". Also, it should be understood that any "optimal" antenna parameters or dimensions described herein are not necessarily absolutely optimal in a mathematical sense. What constitutes "optimal" depends on the criteria used for judging the resulting performance. The antenna parameters identified or selected using techniques described herein represent, at least, a "preferred" set of parameters. Designers may choose to adjust or alter the parameters at their discretion during device design.

For the sake of completeness, an exemplary CRMD will now be described, which includes components for performing controlling pacing and shocking.

Exemplary CRMD

FIG. 10 provides a simplified block diagram, of the CRMD, which in this example is a dual-chamber hybrid device capable of treating both fast and slow arrhythmias with stimulation therapy, including cardioversion, defibrillation, and pacing stimulation. (A single chamber CRMD could instead be used.) To provide atrial chamber pacing stimulation and sensing, CRMD 10 is shown in electrical communication with a heart 612 by way of a right atrial lead 620 having an atrial tip electrode 622 and an atrial ring electrode 623 implanted in the atrial appendage. CRMD 10 is also in electrical communication with the heart by way of a right ventricular lead 630 having, in this embodiment, a ventricular tip electrode 632, a right ventricular ring electrode 634, a right ventricular (RV) coil electrode 15, and a superior vena cava (SVC) coil electrode 638. Typically, the right ventricular lead 630 is transvenously inserted into the heart so as to place the RV coil electrode 15 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, CRMD 10 is coupled to a "coronary sinus" lead 624 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628. With this configuration, biventricular pacing can be performed. Although only three leads are shown in FIG. 9, it should also be understood that additional stimulation leads (with one or more pacing, sensing and/or shocking electrodes) might be used in order to efficiently and effectively provide pacing stimulation to the left side of the heart or atrial cardioversion and/or defibrillation. Alternatively, fewer leads or electrodes might be used. In particular, in many embodiments, no LA coil 628 is included. Note that a portion 13 of CRMD 10 represents the header of the device (to which the leads are connected.) Within the header, the aforementioned inverted E antenna is mounted.

Figure 11:
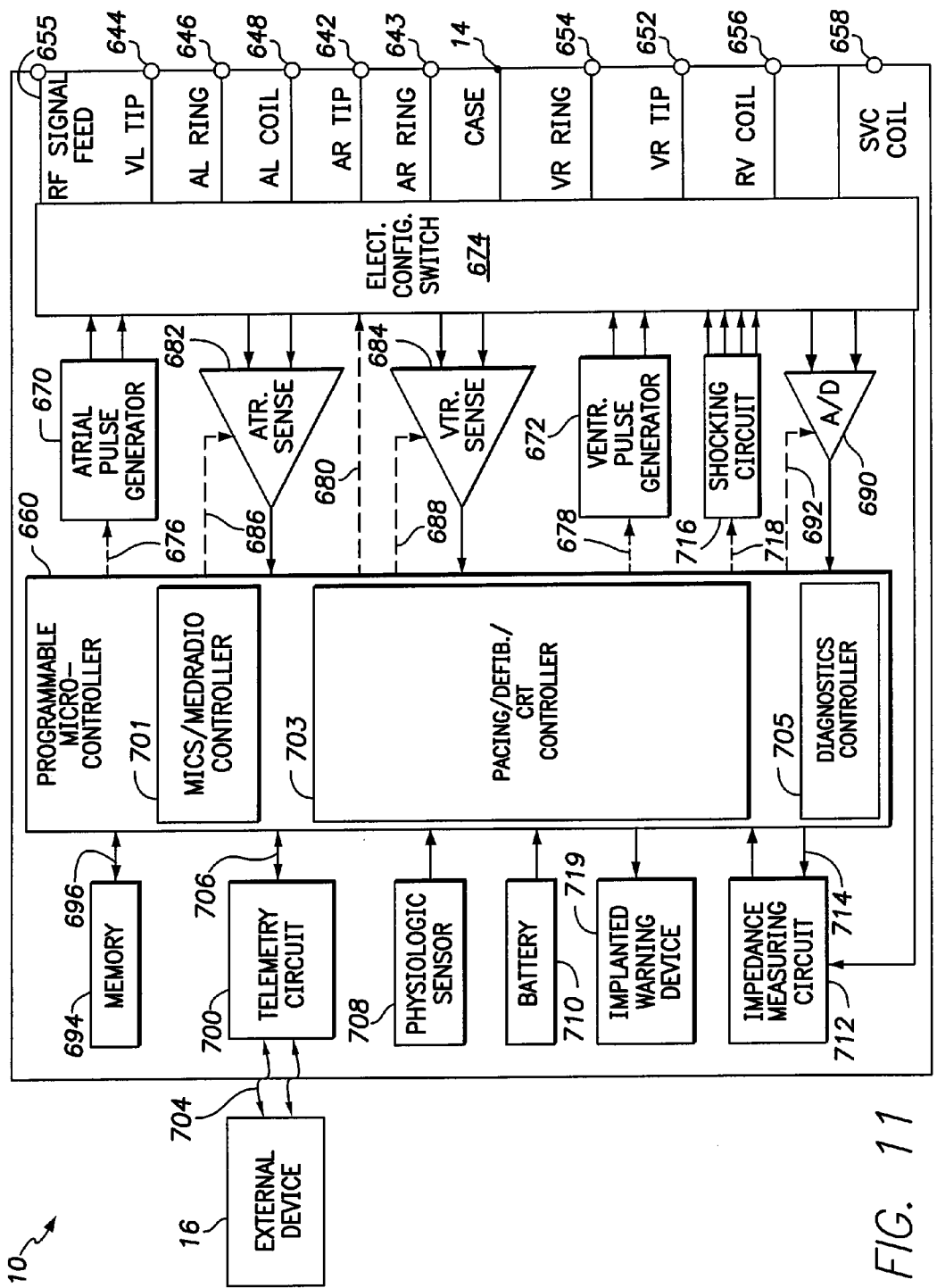
FIG. 11 is a functional block diagram of the CRMD of FIG. 10, illustrating basic circuit elements that provide cardioversion, defibrillation and/or pacing stimulation in the heart, as well as components for MICS/MedRadio communication.

A simplified block diagram of internal components of CRMD 10 is shown in FIG. 11. While a particular CRMD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 14 for CRMD 10, wherein the housing is shown schematically in FIG. 11, is often referred to as the "can", "case" or "case electrode" and may be programmably selected to act as the return electrode for all "unipolar" modes. The housing 14 may further be used as a return electrode alone or in combination with one or more of the coil electrodes, 628, 15 and 638, for shocking purposes and, as noted above, may be used as the ground plane for the antenna of the device. Note that the diagram of FIG. 11 does not illustrate the aforementioned inverted E antenna, which is illustrated within figures already described. The housing 14 includes a connector (not shown) having a plurality of terminals, 642, 643, 644, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 626, the left atrial tip electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($R_V$ COIL) 656, and an SVC shocking terminal (SVC COIL) 658, which are adapted for connection to the right ventricular tip electrode 632, right ventricular ring electrode 634, the RV coil electrode 15, and the SVC coil electrode 638, respectively. Still further, RF signal feed terminal 655 is provided for connection to the RF signal feed branch of the inverted E antenna. The inductive and capacitive branches of the antenna are connected to case 14, as already explained.

At the core of CRMD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 11, an atrial pulse generator 670 and a ventricular/impedance pulse generator 672 generate pacing stimulation pulses for delivery by the right atrial lead 620, the right ventricular lead 630, and/or the coronary sinus lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, coronary sinus lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables CRMD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, CRMD 10 utilizes the atrial and ventricular sensing circuits, 682 and 684, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the coronary sinus lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of CRMD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable CRMD 10 may be non-invasively programmed into the memory 694 through a telemetry circuit 700 in telemetric communication with the external device 16, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of CRMD 10 (as contained in the microcontroller 660 or memory 694) to be sent to the external device 16 through an established communication link 704. Depending upon the implementation, the telemetry circuit may exploit MICS/MedRadio components connected to the inverted E antenna to facilitate telemetry. CRMD 10 further includes an accelerometer or other physiologic sensor 708, commonly referred to as a "rate-responsive" sensor because it is typically used to adjust pacing stimulation rate according to the exercise state of the patient. However, physiological sensor 708 may further be used to detect changes in cardiac output, changes in the physiological condition of the heart, or diurnal changes in activity (e.g., detecting sleep and wake states) and to detect arousal from sleep. Accordingly, microcontroller 660 responds by adjusting the various pacing parameters (such as rate, AV Delay, V-V Delay, etc.) at which the atrial and ventricular pulse generators, 670 and 672, generate stimulation pulses. While shown as being included within CRMD 10, it is to be understood that physiologic sensor 708 may also be external to CRMD 10 yet still be implanted within or carried by the patient. A common type of rate responsive sensor is an activity sensor incorporating an accelerometer or a piezoelectric crystal, mounted within the housing of the CRMD. Other types of physiologic sensors are known including, for example, sensors that sense the oxygen content of blood, respiration rate and/or minute ventilation, pH of blood, ventricular gradient, pulmonary artery pressure, etc.

The CRMD additionally includes a battery 710, which provides operating power to all of the circuits shown in FIG. 11. The battery 710 may vary depending on the capabilities of CRMD 10. If the system only provides low voltage therapy, a lithium iodine or lithium copper fluoride cell may be utilized. For CRMD 10, which employs shocking therapy, the battery 710 must be capable of operating at low current drains for long periods, and then be capable of providing high-current pulses (for capacitor charging) when the patient requires a shock pulse. The battery 710 must also have a predictable discharge characteristic so that elective replacement time can be detected. Accordingly, CRMD 10 is preferably capable of high voltage therapy and appropriate batteries.

As further shown in FIG. 11, CRMD 10 is shown as having an impedance measuring circuit 712, which is enabled by the microcontroller 660 via a control signal 714. The impedance circuit may be used for detecting thoracic and/or cardiogenic impedance. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; detecting the opening of heart valves. The impedance measuring circuit 712 is advantageously coupled to the switch 674 so that any desired electrode may be used.

In the case where CRMD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a high voltage shocking circuit 716 by way of a control signal 718. The shocking circuit 716 generates shocking pulses of low (up to 0.5 joules), moderate (0.5-10 joules) or high energy (11 to 40 joules or more), as controlled by the microcontroller 660. Such shocking pulses are applied to the heart of the patient through at least two shocking electrodes, and as shown in this embodiment, selected from the left atrial coil electrode 628, the RV coil electrode 15, and/or the SVC coil electrode 638. The housing 14 may act as an active electrode in combination with the RV electrode 15, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 6-40 joules or more), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Microcontroller 660 also includes various components directed to controlling MICS/MedRadio communication, defibrillation and diagnostics. Briefly, a MICS/MedRadio controller 701 controls MICS/MedRadio communications using the aforementioned inverted E antenna, as described above. (The inverted E antenna, which is mounted within a header of the device, is not specifically shown in FIG. 11.) A controller 703 controls delivery of pacing, defibrillation shocks, CRT or other therapies depending upon the capabilities of the device. Diagnostics pertinent to MICS/MedRadio communications, defibrillation or any other functions of the device may be generated under the control of diagnostics controller 705 for storage within memory 694 for transfer to an external device.

Depending upon the implementation, the various components of the microcontroller of the implanted device may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. An implantable medical device for implant within a patient, the device comprising:
   a case;
   radio frequency (RF) communication components housed within the case;
   a header mounted to an exterior surface of the case, the header being disposed only along a single edge of the case; and
   an antenna coupled to the RF communication components, the antenna having an inverted E shape, wherein the inverted E shaped antenna is fitted within the header;
   wherein the inverted E shaped antenna has three branches with each of the three branches terminating at respective points on the single edge of the case underneath the header, wherein a first branch of the antenna is capacitive, a second branch provides an RF signal feed and a third branch provides a shunt to ground;
   wherein the case provides a ground plane for the antenna;
   wherein the first branch includes a capacitor mounted in series between a distal end of the first branch and a center arm of the antenna with the distal end of the first branch coupled to the case of the device;
   wherein the capacitor is formed as a parallel plate and mounted via a dielectric to the case of the device.

2. The device of claim 1 wherein a capacitance provided by the parallel plate is set based on the size of the plate, a distance from the plate to the case and electrical characteristic of the dielectric.

3. The device of claim 1 wherein the dielectric includes one or more of an epoxy or another plastic material.

4. The device of claim 1 wherein the second branch of the antenna is coupled to the RF communication components within the case via a respective feedthrough of a feedthrough assembly.

5. The device of claim 1 wherein an impedance of the antenna is set based on a location of the second branch relative to the first and third branches of the antenna.

6. The device of claim 1 wherein an inductance of the third branch is set based on a length of the third branch.

7. The device of claim 1 wherein a resonant frequency of the antenna is adjustable based on one or more of: relative lengths of the first, second and third branches; a capacitance of the first branch; a location of the second branch relative to the third branch and a cross-sectional area of conducting elements forming the components of the antenna.

8. The device of claim 1 wherein a capacitance of the first branch is set relative to an inductance of the antenna to provide substantially no reactance.

9. The device of claim 1 wherein an input impedance of the antenna is substantially equal to a complex conjugate of an impedance of the RF frequency components.

10. The device of claim 1 wherein the implantable medical device is a cardiac rhythm management device.

11. The device of claim 1 wherein the RF components include one or more of Medical Implant Communication Service (MICS) components and Medical Device Radiocommunications Service (MedRadio) components.

12. An implantable medical device for implant within a patient, the device comprising:
    a case;
    pulse generating circuitry housed within the case;
    radio frequency (RF) communication components housed within the case;
    a header mounted to an exterior surface of the case, the header enclosing a feedthrough assembly and connectors for receiving electrical leads for electrical connection to the pulse generating circuitry, the header being disposed only along a single edge of the case; and
    an antenna coupled to the RF communication components, the antenna having an inverted E shape, wherein the inverted E shaped antenna is fitted adjacent to an outer edge of the header and substantially circumscribes a path about the connectors within the header;
    wherein the inverted E shaped antenna has three branches with each of the three branches terminating at respective points on the single edge of the case underneath the header, wherein a first branch of the antenna is capacitive, a second branch provides an RF signal feed and a third branch provides a shunt to ground;

wherein the case provides a ground plane for the antenna;

wherein the first branch includes a capacitor mounted in series between a distal end of the first branch and a center arm of the antenna with the distal end of the first branch coupled to the case of the device;

wherein the capacitor is formed as a parallel plate, mounted via a dielectric to the case of the device, and located at a portion of the header opposite to a portion of the header where the feedthrough assembly is located.

13. The device of claim 12 wherein a capacitance provided by the parallel plate is set based on the size of the plate, a distance from the plate to the case and electrical characteristic of the dielectric.

14. The device of claim 12 wherein the dielectric includes one or more of an epoxy or another plastic material.

15. The device of claim 12 wherein the second branch of the antenna is coupled to the RF communication components within the case via a respective feedthrough of the feedthrough assembly.

16. The device of claim 12 wherein an impedance of the antenna is set based on a location of the second branch relative to the first and third branches of the antenna.

17. The device of claim 12 wherein an inductance of the third branch is set based on a length of the third branch.

18. The device of claim 12 wherein a resonant frequency of the antenna is adjustable based on one or more of: relative lengths of the first, second and third branches; a capacitance of the first branch; a location of the second branch relative to the third branch and a cross-sectional area of conducting elements forming the components of the antenna.

19. The device of claim 12 wherein a capacitance of the first branch is set relative to an inductance of the antenna to provide substantially no reactance.

20. The device of claim 12 wherein an input impedance of the antenna is substantially equal to a complex conjugate of an impedance of the RF frequency components.

* * * * *